US005767095A

United States Patent [19]

Winget

[11] Patent Number: 5,767,095
[45] Date of Patent: *Jun. 16, 1998

[54] ANTI-INFLAMMATORY COMPOSITIONS CONTAINING MONOGALACTOSYL DIEICOSAPENTAENOYL GLYCEROL AND METHODS RELATING THERETO

[76] Inventor: Rodner R. Winget, 13265 89th Ave. South, Rte. 3, Renton, Wash. 98055-1930

[*] Notice: The term of this patent shall not extend beyond the expiration date of Pat. No. 5,620,962.

[21] Appl. No.: 779,783

[22] Filed: Jan. 7, 1997

Related U.S. Application Data

[63] Continuation of Ser. No. 484,832, Jun. 7, 1995, Pat. No. 5,620,962, which is a continuation-in-part of Ser. No. 55,533, Apr. 30, 1993, abandoned.

[51] Int. Cl.$^6$ .................................................. A61K 31/70
[52] U.S. Cl. .............................. 514/25; 514/886; 514/887
[58] Field of Search ............................. 514/25, 886, 887

[56] References Cited

U.S. PATENT DOCUMENTS 5,620,962  4/1997  Winget ........................................ 514/25

OTHER PUBLICATIONS

David. A. Mannock et al, "The Physical Properties of Glycosyldiacylglycerols. Calaorimetric Studies of a Homologous Series of 1,2-Di-O-acyl-3-(-B-D-glucopyranosyl) sn-glycerols", *Biochem.*, 27:6852–6859, 1988.

*Primary Examiner*—Cecilia J. Tsang
*Assistant Examiner*—Abdel A. Mohamed
*Attorney, Agent, or Firm*—Janet Sleath

[57] ABSTRACT

Disclosed are topical anti-inflammatory compositions containing 0.1% to 10% by weight of a monogalactosyl dieicosapentaenoyl glycerol having esterified eicosapentaenoic acid residues (MGDG-EPA); anti-inflammatory compositions are formulated using a purified microalgal lipid preparation containing 30% to 100% by weight of MGDG-EPA; methods of making the microalgal lipid preparation; methods of treating inflammation by administering the topical anti-inflammatory compositions to a subject in need thereof.

15 Claims, 3 Drawing Sheets

ANTI-INFLAMMATORY COMPOSITIONS CONTAINING MONOGALACTOSYL DIEICOSAPENTAENOYL GLYCEROL AND METHODS RELATING THERETO

This application is a continuation application of Ser. No. 08/484,832 filed Jun. 7, 1995 now U.S. Pat. No. 5,620,962, as a continuation-in-part application of Ser. No. 08/055,533 (filed Apr. 30, 1993 now abandoned.)

FIELD OF THE INVENTION

The invention relates generally to anti-inflammatory compositions and, more specifically, to anti-inflammatory compositions derived from marine algae having a high content of monogalactosyl dieicosapentaenoyl glycerol (MGDG-EPA.)

BACKGROUND OF THE INVENTION

Monogalatosyldiacylglycerides (MGDG) may generally be obtained from a number of higher plant sources including vegetables such as lettuce, broccoli, wheat and alfalfa, as well as from the central nervous system tissues of animals, and from a variety of macro- and micro-marine algae. However, monogalactosyldiacylglycerides containing the polyunsaturated fatty acid cicosapentaenoic acid (i.e., EPA) are only found in marine algae. More specifically, monogalactosyl diacyl glycerides (i.e., MGDG) with the highest content of eicosapentaenoic acid are found in cold water marine micro-algae species. These eicosapentaenoic acid containing glycerides (i.e., MGDG-EPA) are synthesized along with many other algal products (e.g., pigments, phospholipids, and other glyceryl lipids such as sulphoquinovosyldiacylglycerides, abbreviated SQDG, and diacylglyceryl-N,N,N-trimethylhomoserine, DGTS), thus making the reproducible isolation of useful quantities of high purity compositions complex and burdensome. Purity is particularly important for pharmaceutical and cosmetic compositions because chlorophylls and glycerolipids with similar solubilities may exhibit undesirable properties, e.g., potentiation of inflammation.

The therapeutic potential of EPA has fascinated medical scientists for more than two decades (1). There is continued interest in whether polyunsaturated fatty acids act as precursors of eicosanoid cascade-derived second messengers in inflammation or function via mechanisms independent of these messengers, e.g., by cytokine inhibition (2). Until recently, EPA used in studies of inflammation has been a free acid or sodium salt, a methyl or ethyl ester, or a component of fish oil or dietary fish, primarily in the form of triacylglycerols. Studies have generally employed EPA compounds delivered systemically, generally by ingestion, or have related to in vitro assays. Investigations with these EPA compounds have led to a 'substrate substitution hypothesis' according to which EPA may take its effects by (i) transfer of EPA from applied lipids to cell membrane phospholipids (3); (ii) release of free EPA from putative membrane storage deposits through the action of phospholipases (4), and, (iii) substitution of EPA for arachidonic acid (AA) in metabolism with resultant production of less effective (or lower levels of) inflammatory mediators (5,6). At odds with this hypothesis is a preliminary report by Krueger et al. who found anti-inflammatory activity associated with an acylated-EPA, (in an amphiphilic lipid extracted from marine microalgae) and also an acylated-AA analogue of the algal lipid (7). The reported activity of the acylated-AA is difficult to accord with the substrate substitution hypothesis, since metabolism of acylated-AA would be expected to result in release of appropriate inflammatory mediators. However, the inflammation may be triggered through multiple different pathways, including at least bradykinin system proteins, complement and coagulation activation fragments, factors released from platelets such as platelet factor 4, and mediators of immediate type hypersensitivity, e.g., serotonin and histamine. Also, once triggered inflammation is propagated through the action of integrin-adhesin interactions, endothelial cell factors, and other serum factors. Thus, while EPA may serve as a substrate in AA metabolic pathways, it is presently unclear what compositions might be used topically to prevent or inhibit epithelial inflammation.

SUMMARY OF THE INVENTION

Disclosed herein are findings indicating that topical anti-inflammatory activity of microalgal lipids containing MGDG-EPA is dependent upon at least three factors: namely, (i) the type of glycerol-sugar backbone (i.e., galacto-lipid e.g., MGDG or digalactosyldiacylglycerol, abbreviated DGDG), (ii) the nature of the fatty acid acylation and the degree of unsaturation (i.e., 20:5); and, (iii) the degree of purity. It was discovered that microalgal lipid preparations can contain contaminants (e.g., at least chlorophyll and diacylglyceryl-N,N,N-trimethylhomoserine, DGTS). DGTS can promote, rather than inhibit, inflammation; even when present as only 2% by weight of a topical preparation. Chlorophyll has been reported to have clastogenic properties. Topical anti-inflammatory compositions and processes for preparation of same using highly purified microalgal lipids are disclosed.

In one embodiment the invention provides a topical anti-inflammatory composition comprising about 0.1% (w) to about 10% (w) of an MGDG-EPA in a delivery vehicle. The composition has less than 2% of other microalgal contaminants, and particularly less than 2% of DGTS.

In another embodiment, the invention provides a process of manufacturing an anti-inflammatory microalgal lipid preparation enriched in MGDG-EPA (i.e., 35–100% pure) and containing low levels of contaminants. The process includes the steps of extracting marine algae; phase separating to yield an organic phase; fractionating the organic phase using first, polar chromatography; followed by, non-polar chromatography or a second polar chromatography ; followed by solvent removal to yield the microalgal lipid preparation useful in formulating the topical anti-inflammatory compositions.

In another embodiment, the invention provides a method for treating inflammation comprising topically administering to an animal, including humans, an anti-inflammatory composition containing about 0.1%–10% of MGDG-EPA as formulated using a highly purified microalgal lipid preparation having a high content of MGDG-EPA. The composition may be administered in various forms, including emollients, ointments, capsules, tablets, drops, syrup, lozenges, suppositories, inclusions and aerosols.

Other aspects of the present invention will become evident upon reference to the attached figures and following detailed description.

Fractions 40-I, 40-II and 60 contain DGTS-EPA. Lane 1, MGDG Std.; 2, 10;3, 20-I; 4, 20-II; 5, 20-III; 6, 40-I; 7, 40-II; 8, 60; 9, 100; 10, MeOH; 11, MGDG-Std; 12, DGTS-Std. Position A, chlorophyll; B, xanthopyll; C, MGDG-EPA; D, DGTS; E, DGDG; F, phospholipids.

Figure 3:
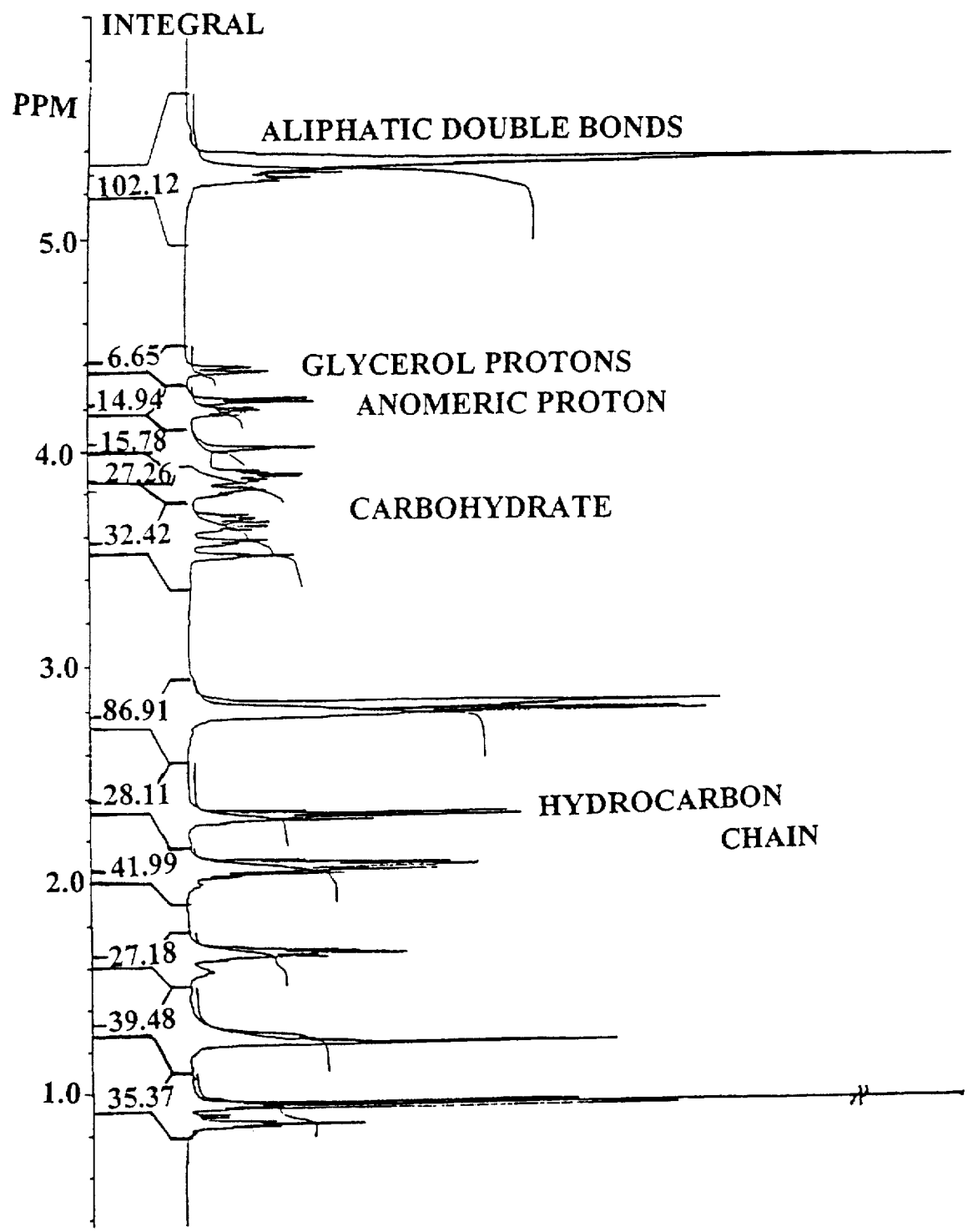

FIG. 3 presents the proton NMR spectra for MGDG-EPA as present in a representative microalgal lipid preparation:

SF, 500.135; Sy, 60.0; 01, 7400.000; SI, 16384; TD, 16384; SM, 6024.096; Hz/PT, 0.735; PM, 12.0; RD, 1.000; AQ, 1.360; RG, 128; NS, 8; TE, 297; FW, 7600; 02, 29435.885; DP, 20L PO; LB, 0.0; GB, 0.0; CX, 34.00; CY, 0.0; Fl, 6.000P; F2, 0.363 P; HZ/CM, 82.923; PPM/CM, 0.166; SR, 5436.00.

DETAILED DESCRIPTION ON THE INVENTION

Embodiments of the invention provide anti-inflammatory compositions containing 0.1–10% MGDG-EPA and formulated using both a purified microalgal lipid preparation having 35–100% MGDG-EPA and with low levels of contaminants, and a vehicle.

As used herein the following terms are intended to have meaning as follows: namely, "Anti-inflammatory composition" and "composition" are intended to mean pharmaceutical compositions formulated and compounded with a vehicle. Representative compositions include emollients, ointments, capsules, tablets, drops, syrup, lozenges, suppositories, inclusions, aerosols, and the like.

"Microalgal lipid preparation" and "preparation" are intended to mean lipid preparations purified from biological samples. Representative preparations include MGDG-EPA microalgal lipid preparation, EPA ethyl ester, fish oil and the like.

As used herein, "MGDG-EPA" is intended to mean a monogalactosyl dieicosapentaenoyl glycerol wherein at least one of the acyl moieties is an eicosapentaenoic acid residue esterified to the glycerol backbone, as represented by the following structure I: namely,

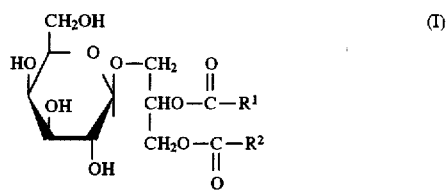

1,2-diacyl-(β-D-galactopyranosyl(1'→3))-sn-glycerol wherein $R^1$ and $R^2$ represent a hydrocarbon chain of fatty acids containing from 10 to 25 carbon atoms and from 0 to 6 carbon-carbon double bonds, and wherein at least $R^1$ or $R^2$ is the hydrocarbon chain of eicosapentaenoic acid. MGDG-EPA is present in the composition in an amount ranging from 35 to 100 percent by weight of the total composition. In a preferred embodiment, both $R^1$ and $R^2$ are the hydrocarbon chain of eicosapentaenoic acid.

As used herein "DGDG" is intended to mean a digalactosyl-diacylglycerol as represented by the following structure II: namely,

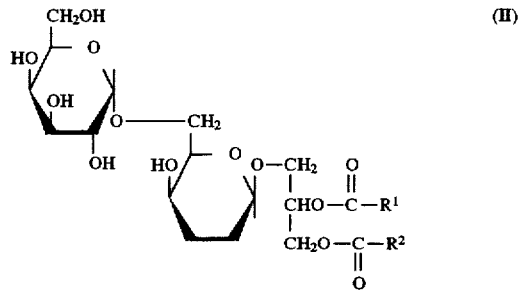

1,2-diacyl-(α-D-galactopyranosyl-(1'→6)-β-D-galactopyranosyl-(1'→3))-sn-glycerol wherein $R^1$ and $R^2$ represent the hydrocarbon chain of a fatty acid containing from 10 to 25 carbon atoms and from 0 to 6 carbon-carbon double bonds. In addition, the anti-inflammatory compositions of the present invention may further comprise phosphatidyl choline ("PC"), as well as chlorophylls and carotenoids.

As used herein, "DGTS-EPA" and "DGTS" are used interchangeably to mean diacylglyceryl-N,N,N-trimethylhomoserine, as represented by the following structure III: namely,

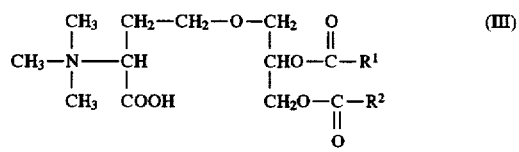

Embodiments of the invention provide topical anti-inflammatory compositions formulated from a high purity microalgal lipid preparation with a high content of MGDG-EPA, and, in addition, lacking in contaminants capable of inducing adverse reactions, in this case, other microalgal lipids capable of potentiating ongoing inflammatory responses.

"Microalgal lipid preparation" as used herein is intended to mean a purified organic extract of an algae selected from the genera consisting of Chlorella, Chaetoceros, Cyclotella, Isocarysis, Nannochloropsis, Nitzschia and Phyaeodactylum, that contains high content, e.g., 35–100% percent by weight (as disclosed further below), of a monogalactosyl dieicosapentaenoyl glycerol according to structure I, above, and less than about 65% total weight of one or more contaminants that are selected from among diacylglyceryl-N,N,N-trimethylhomoserine (structure III), chlorophylls, carotenoid, sterols, SQDG, and phospholipids (i.e., phosphatidyl serine, phosphatidyl ethanolamine, and phosphatidyl choline). The subject microalgal lipid preparation may optionally contain DGDG (according to structure II, above).

Figure 1:
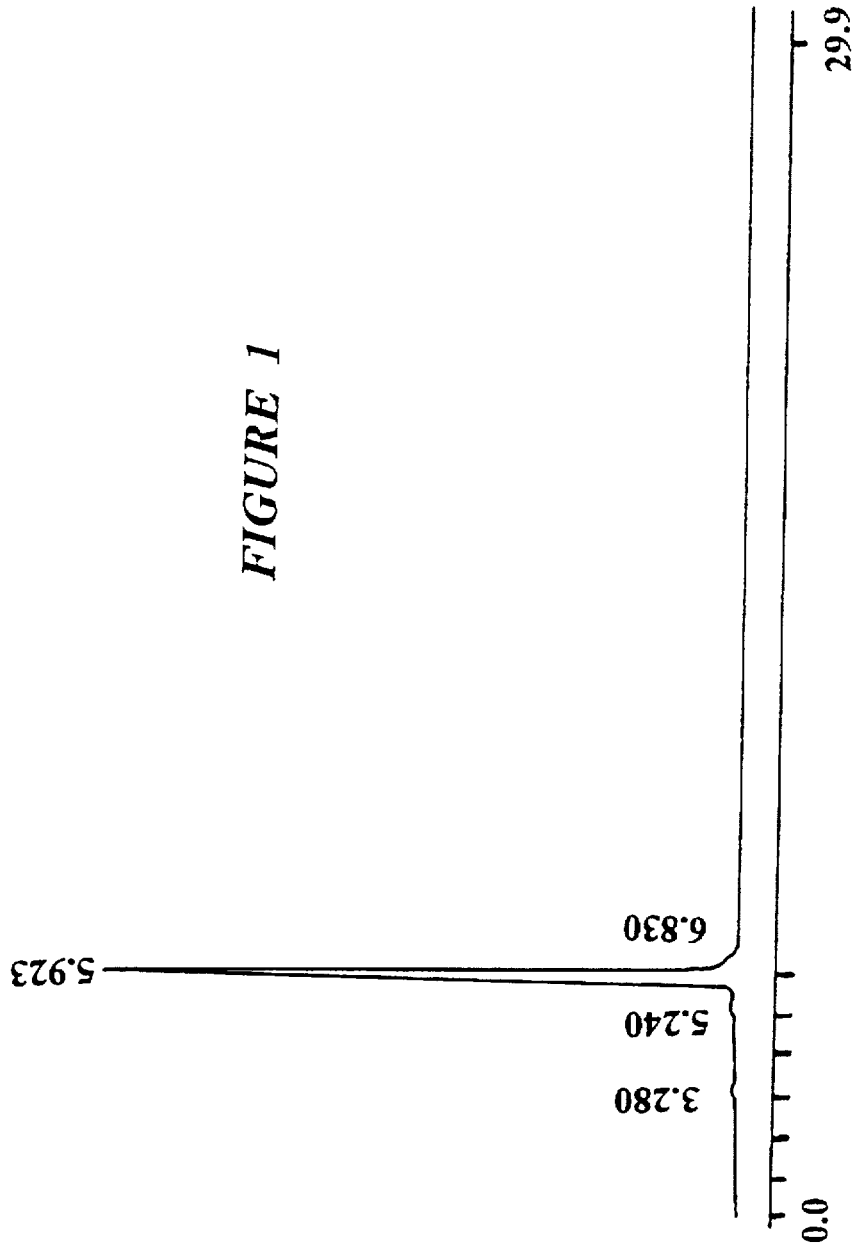
FIG. 1 depicts the tracing of a chromatographic separation of a representative microalgal lipid preparation according to the invention, in this case illustrating the components as resolved by high performance liquid chromatography (HPLC) on a Microsorb-Si column in methanol liexane at a flow rate of 0.5 ml/min. and detected: "3.280", "5.240", "5.923", and "6.830" are the elution times for the major components detectable. The microalgal lipid preparation depicted in the figure was fraction 20-III (i.e., the 20% ethanol in hexane fraction) from silicic acid column chromatography as described in Example 2, below. Fraction 20-III had greater than 95% by weight of MGDG-EPA and less than about 5% of contaminants that included DGTS-EPA (peak 4), chlorophylls (peak 1), carotenoids (peak 2), and DGDG (below the levels of the HPLC detector.) The composition of fraction 20-III is further depicted in FIG. 2, below.

Preferably the algal extract is an organic extract from the species consisting of Chaetoceros gracillis , Chaetoceros muelleri Cyclotella cryptica , Isochrysis galbana , Nannochloropsis salina Nitzschia dissipata and Phyaeodactylum tricornutum. Illustrative microalgal lipid preparations appear in the total high performance liquid chromatogram depicted in FIG. 1 and in the thin layer chromatogram of the microalgal lipid preparation FIG. 2 (i.e., fractions "20-II"and "20-III").

MGDG-EPA is identified above as structure I wherein $R^1$ and $R^2$ represent a hydrocarbon chain of a fatty acid, and wherein at least $R^1$ or $R^2$ is the hydrocarbon chain of eicosapentaenoic acid ("EPA" - an omega-3 fatty acid containing 20 carbon atoms and 5 double bonds). For example, when $R^2$ of structure I is the hydrocarbon chain of a non-EPA fatty acid, the corresponding MGDG-EPA has the following structure IV: namely,

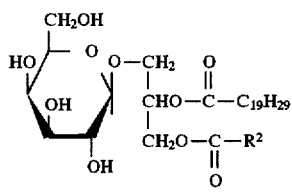

1,2-diacyl-(β-D-galactopyranosyl(1'→3))-sn-glycerol wherein $R^2$ represent a hydrocarbon chain of fatty acids containing from 10 to 25 carbon atoms and from 0 to 6 carbon-carbon double bonds.

Similarly, when both $R^1$ and $R^2$ of structure I are the hydrocarbon chain of EPA, the corresponding MGDG-EPA is of the following structure V: namely,

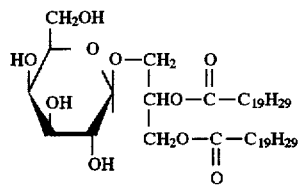

As used herein the term "fatty acid" is intended to mean members of a class of organic compounds containing a saturated or unsaturated, branched or unbranched, substituted or unsubstituted, hydrocarbon chain which terminates in a carboxyl group. The hydrocarbon chains of the fatty acids of the present invention preferably contain from 10 to 25 carbon atoms and from 0 to 6 carbon-carbon double bonds, and more preferably from 12 to 22 carbon atoms. Representative examples of fatty acids include (but are not limited to) lauric acid (12:0), myristic acid (14:0), palmitic acid (16:0), stearic acid (18:0), oleic acid (18:1), eicosapentaenoic acid (20:5), and docosahexaenoic acid (22:6) wherein the first number in parenthesis refers to the number of carbon atoms in the hydrocarbon chain, and the second number refers to the number of double bonds.

In a preferred embodiment of MGDG-EPA, both $R^1$ and $R^2$ of structure I (above) are the hydrocarbon chain of EPA. In a further preferred embodiment, the carbon-carbon double bonds of EPA are located at the Δ5, 8, 11, 14 and 17 positions (i.e., cis-Δ-5, 8, 11, 14, 17-eicosapentaenoic acid).

As defined above, the "microalgal lipid preparations" of the instant invention contain a high content of MGDG-EPA. Specifically, the preparation contains MGDG-EPA in an amount ranging from 35 to 100 percent by weight of the total preparation, preferably about 85 to 94 percent by weight of the total preparation, and most preferably from 95 to 100 percent by weight of the total preparation. In addition to the values specifically identified above, all values for MGDG-EPA falling within the above ranges are expressly incorporated herein. In addition, all of the subject preparation contain less than about 65% by weight of contaminants including DGTS, chlorophylls, carotenoids, and phospholipids. In a presently most preferred microalgal lipid preparation the preparation by weight is about 95% MGDG-EPA, 3% DGTS, less than 2% carotenoids and chlorophylls, with traces of phospholipids.

In an alternative embodiment, the invention provides a topical anti-inflammatory composition formulated from about 0.1–10% by weight of a DGDG-lipid preparation, e.g., a DGDG-microalgal lipid preparation containing a high content and purity of DGDG. The subject DGDG is as identified in structure II, wherein $R^1$ and $R^2$ represent the hydrocarbon chain of a fatty acid containing from 10 to 25 carbon atoms and from 0 to 6 carbon-carbon double bonds. DGDG may be present in the DGDG-microalgal lipid preparation in an amount up to about 20% to about 100% by weight of the total preparation, and the preparation may optionally contain MGDG-EPA.

Embodiments of the invention provide highly purified "microalgal lipid preparations", as defined above, that contain both a high content and purity of MGDG-EPA and less than 65% (w) of microalgal contaminants. Preferably the microalgal lipid preparation contains less than about 10% (w) of the DGTS, identified in structure III, above, and most preferably the amount of DGTS is less than about 5% (w).

The subject microalgal lipid preparations are useful for formulating the subject topical anti-inflammatory compositions of the invention. In addition to MGDG-EPA and low levels of contaminants, the microalgal lipid preparations of the present invention may optionally include DGDG and phospholipids. In total, the microalgal lipid preparation according to the invention contains a cumulative amount of DGTS, phospholipids, chlorophylls and/or carotenoids that is less than 65% by weight of the subject preparation.

Eicosapentaenoic acid ("EPA") is present as a constituent, in an esterified form, of the monogalactosyl dieicosapentaenoyl glycerol of the instant invention. According to the classical "substrate-substitution hypothesis" of action for EPA compounds, anti-inflammatory activity of MGDG-EPA would result following metabolic release of EPA from MGDG-EPA, and the EPA so released would presumptively enter cellular phospholipid pools and function as substrates in arachidonic acid (AA) metabolic pathways, also known as the eicosanoid pathway. When inflammation is triggered phospholipase $A_2$ is activated and AA or EPA is released from cellular phospholipids. The eicosanoid pathway involves two enzymes that catalyze metabolism of AA to prostaglandins, thromboxanes, leukotrienes, and prostacyclins which have inflammatory activity. EPA shares structural similarities with AA and may reportedly be used as a substrate. The possibility that EPA may substitute for AA in the eicosanoid pathway gives rise to a hypothesis referred to herein as the "substrate substitution hypothesis". EPA has 5 unsaturated double bonds while AA has only 4. The extra double bond is reportedly retained in the metabolites of EPA, and such altered metabolites reportedly exhibit lower inflammatory activity than natural AA metabolites in certain assays. EPA is also reported to be a competitive inhibitor of an enzyme involved in synthesis of prostaglandins and thromboxanes.

However, in the present animal models of dermal inflammation, topically applied EPA preparations (i.e., Fish oil, EPA ethyl ester, and DGTS-EPA) did not exhibit anti-inflammatory activity within the range of concentrations tested (EXAMPLE 4). In contrast, the subject topical preparations of the instant invention containing microalgal MGDG-EPA lipids exhibited anti-inflammatory activity at the same concentration. Since the substrate-substitution hypothesis predicts the existence of a pool of cellular EPA-phospholipid substrates, studies were conducted to isolate, purify and identify EPA in the skin treated for 26 weeks with the subject MGDG-EPA microalgal lipid preparations. Interestingly, using sensitive analytical methodology capable of detecting EPA (i.e., GC), if it were present, it was at levels no higher than in the vehicle-treated control animals (EXAMPLE 4). In other studies, phospholipids acylated with AA, were at 16% (w) found to exhibit an anti-inflammatory activity that would not be predicted by a substrate-substitution hypothesis (i.e., AA should be inflammatory).

Histologic studies were conducted of tissues in which inflammation was inhibited by topical application of MGDG-EPA containing microalgal lipids. These samples failed to show any significant signs of neutrophil infiltration in the tissues or pavementing in the microvasculature, as if the induction phase of inflammation was inhibited. In considering possible mechanisms that might account for these combined findings, attention was directed to the cell biology of the epithelium and events that might be involved in the induction phase of inflammation. The preceding observations provoked consideration of a novel, heretofore unreported approach to considering anti-inflammatory treatments using amphiphilic lipids.

While not wishing to be tied to any particular mechanism, it is reasoned that to induce inflammatory cells to enter an inflammatory site, i.e., by extravasation through endothelial junctions, requires at least the actions of chemotactic agents and integrin-adhesin interactions. Next, it is necessary that to "trigger" neutrophil activation, e.g., through the action of chemokine receptor-mediated signal transduction, calcium channel flux changes, and/or changes in cyclic nucleotides, with changes in cellular phosphorylases and protein kinases. The subject microalgal MGDG-EPA lipids are amphiphilic galactolipids. It is believed likely that the polar character of MGDG-EPA allows more ready integration into membranes than EPA, or compounds like EPA ethyl ester or fish oil triglycerides. The highly unsaturated nature of MGDG-EPA may also aid membrane insertion compared with other forms of MGDG. It is presently believed likely that membrane integrated MGDG-EPA may interfere with the induction phase of inflammatory responses, perhaps by interfering with or down-regulating signal transduction triggered by cytokines, chemokines, or integrin-adhesin receptor binding interactions. Thus, it is presently considered likely that these lipids become integrated in the mammalian cell membrane where the long-chain highly unsaturated EPA fatty acids may alter membrane dynamics, and particularly those events involved in triggering of signal transduction. Thus, it is believed likely that MGDG-EPA act to inhibit receptor-mediated signal transduction, calcium channel flux changes and/or changes in adenylate cyclase activity that lead to subsequent changes in cellular cyclic nucleotide levels (e.g., cAMP/cGMP), cellular protein kinase activity (e.g., Protein Kinase C), and eventually, to altered activity of phospholipase $A_2$. The latter model differs significantly in form and substance from a substrate-substitution hypothesis, both in mechanisms and in the extension to different pharmaceutical compositions and therapeutic uses. For instance, if the aim of a pharmaceutical composition is to supply sufficient EPA to saturate a putative cellular pool of phospholipids, then a high dose of any particular EPA type might be incorporated into the composition, e.g., a high concentration of fish oil. If on the other hand, the aim is to subtly alter membrane lipid content, then a lower dose, e.g., 0.1–10% by weight, and a different lipid, i.e., MGDG-EPA, might be appropriate. The lower doses have clear advantages to the patient, not the least of which is the now recognized risk of adverse reactions complicated by the possible presence of DGTS in lipid preparations.

Embodiments of the invention provide pharmaceutical compositions containing 0.1–10% MGDG-EPA. The subject compositions may be topically administered either prophylactically or therapeutically to prevent or treat inflammation in a host in need thereof The subject composition is formulated using a highly purified (i.e., 35–100% pure) MGDG-EPA containing microalgal lipid preparation. Purity is a key element in avoiding potential adverse patients reactions according to the methods of the invention. The relationship between MGDG-EPA purity and the levels of contaminating lipids is illustrated in TABLE A, below, using e.g., a formulation consisting of 100 grams of a topical cream with 10% MGDG-EPA by weight. For example, 10 gm of MGDG-EPA in 100 gm of the composition would require incorporation of a microalgal lipid preparation into the formulation that was 90% pure in order to achieve a contaminant concentration of 1% by weight of the composition. On the other hand, I gm of MGDG-EPA in 100 gm of composition would require a lipid purity of 50% MGDG-EPA to achieve a contaminant concentration of 1% by weight of the composition.

TABLE A

Formulation of an Illustrative Composition Comprising 10% by Weight of MGDG—EPA and Preparation Having a Purity in the Range of 35–90% (w)

| Desired Weight % MGDG—EPA[a] (gm/100 gm) | MGDG—EPA Preparation. | | | Weight Percent of Contaminants[b] | Weight % of Vehicle |
|---|---|---|---|---|---|
| | Purity (%) | Preparation (gm/100 gm) | Contaminants (gm/100) | | |
| 10% w | 35 | 28.6 | 18.6 | 18.6% | 71.4 |
| (10 gm/100 gm) | 40 | 25 | 15 | 15% | 75 |
| | 50 | 20 | 10 | 10% | 80 |
| | 60 | 16.7 | 6 | 6% | 84 |
| | 70 | 14.3 | 4 | 4% | 86 |
| | 80 | 12.5 | 2.5 | 2.5% | 87.5 |
| | 90 | 11.1 | 1 | 1% | 89 |

[a]Weight percent in the composition;
[b]Weight of contaminants in the MGDG—EPA composition The subject composition is administered in an amount and for a time sufficient to prevent or diminish flammation. Formulations for topical administration include drops, ointments, creams, lotions, gels, oils, emollients, inclusions and aerosols. Formulation for perosteal administration include tablets, capsules, lozenges, syrups and the like. Topical ministration is effective for preventing or treating localized inflammatory disease. For example, the composition may be administered as an emollient for sunburn, athlete's foot, acne, pruritus, eczema, psoriasis, atopic dermatitis and rheumatoid arthritis. Nonspecific inflammation associated with melanotic skin lesion (i.e., skin cancer) may also prove responsive to the composition of the instant invention, allowing more effective treatments with topically applied anti-cancer drugs. Aerosols of the subject MGDG-EPA microalgal preparation are envisaged for treatment of bronchial inflammation and dermal burns. Bioadhesive delivery system are also envisaged. Bioadhesives, pills, capsules, tablet, lozenges and like formulated with the subject MGDG-EPA microalgal preparation may be used in treating esophagitis or inflammatory bowel diseases, and suppositories may be used for treating rectal inflammation. Drops may be used topically for treatment inflammation of the eyes, ears or nose.

Embodiments of the invention provide a water-washable, anti-inflammatory, pH neutral, emollient gel. The subject emollient consists of the following amounts of agents namely, 0.8–1.2% of the subject MGDG-EPA containing microalgal lipid preparation, 52.2–78.2% deionized water, 0.16–0.24% Carbopol 940NF, 9–13.4% L-Sorbitol, 0.32–0.48% sodium hydroxymethyl glycinate, 5.6–8.4% myristyl proprionate, 3.2–4.8% mineral oil, 0.4–0.6% Aloe Vera oil, 0.06–0.14% retinol palmitate, 0.16–0.24% dl-Tocopheryl acetate, 0.16–0.24% L-ascorbate-6-palmitate, 4.8–7.2% stearic acid, 3.2–4.8% glyceryl monostearate, and trace fragrance. Most preferably the subject emollient consists of the following amounts of agents: namely, 1% of the subject MGDG-EPA containing microalgal lipid preparation, 65.2% deionized water, 0.2% Carbopol 940NF, 11.2% L-Sorbitol, 0.4% sodium hydroxymethyl glycinate, 7.0% myristyl proprionate, 4% mineral oil, 0.5% Aloe Vera oil, 0.1% retinol palmitate, 0.2% dl-Tocopheryl acetate, 0.2% L-ascorbate-6-palmitate, 6% stearic acid, 4% glyceryl monostearate, trace fragrance. Skilled artisans will of course recognize that it will be necessary to alter the amounts of the ingredients, and particularly water, as different amounts of different purities of the MGDG-EPA microalgal lipid preparation are blended into the formulation so that the final concentration of MGDG-EPA will be selected from within the range of 0.1–10% by weight.

The pharmaceutical composition of the present invention is applied to a subject in need thereof at a frequency and at a concentration effective to prevent or treat inflammation. Formulation and compounding of pharmaceutical compositions is known in the art, as are methods for determining effective doses and administration schedules in different subjects in need thereof, e.g., using escalating dose studies. Dosage and schedule will of course depend upon at least the avenue of administration, and the location and severity of inflammation. In the practice of the instant invention, pharmaceutical compositions containing 0.1–10% of MGDG-EPA are applied to a subject in need thereof.

The efficacy of an anti-inflammatory composition according to the instant invention may be verified by an appropriate in vitro or in vivo assay. For example, a presently preferred efficacy assay for a topical anti-inflammatory pharmaceutical composition is inhibition of mouse ear swelling induced by an inflammatory agent such as croton oil. In a propylactic assay, the ears of an experimental animal are treated with the subject composition for one or more days, and then ear swelling is induced in the experimental animal and in a control animal. The difference in ear swelling between the experimental and control animals is one determination of efficacy of an anti-inflammatory composition according to the invention, and is illustrated in Example 3, below.

Anti-inflammatory compositions according to the present invention are formulated from microalgal lipid preparations that are extracted from marine microalgae by extraction, followed by chromatography, i.e., as disclosed in greater detail below. The genera of algae that may be so useful for extraction include (but are not limited to) Chlorella, Chaetoceros, Cyclotella, Ellipsoidon, Isochrysis, Nannochloris, Nannochloropsis, Nizschia, Phyaeodactylum, Porphyridium, Skeletonema, Thalassiosira, Gigartina, Monochrysis and Monoraphidiunm. Preferred species within the above genera include *Chlorella minutissima, Chaetoceros gracillis, Chaetoceros muelleri, Cycolotella cryptica, Isochrysis galbana, Nannochloropsis salina, Nitzschia dissipata,* and *Phyaeodactylum tricornutum.*

The marine algae from which the microalgal lipid preparations of the invention are obtained are first cultured in seed cultures in small vessels (such as 15 L carboys) and then cultured in pilot scale in tanks, bioreactors, or culture ponds. The culture medium may be salinated freshwater or preferably filtered sea water. The medium is preferably supplemented with nutrients, including (but not limited to) ammonium, bicarbonate, phosphate, iron, nitrate and trace minerals. Examples of culture protocols that may be suitable for large scale propagation of the subject microalgae are described in e.g., A. Richmond Ed., *Handdbook of Microalgal Mass Culture*, CRC Press, Boca Raton, FL (1986) (incorporated herein by reference in its entirety). The algae may be harvested when the density of the algal culture is sufficiently high, preferably when the optical density of the algal culture at 690 nm is 1.0. Harvesting may be accomplished by coarse screening of the algal culture and then concentration of the resulting algae. Concentration and removal of water is commonly accomplished using centrifugation, unit gravity sedimentation, evaporation, flocculation, ultrafiltration, flotation, or a combination of these techniques. The resulting dewatered algae are suitable for extraction.

Dewatered algal concentrates (from above) are extracted using "extraction solvent(s)" in a process herein after referred to as "Extraction Protocol A", to yield an "extraction solvent extract". Extraction Protocol A solubilizes microalgal lipids that contain MGDG-EPA. Suitable "extraction solvents" (i.e., "Solvent A") include polar organic solvents such as alcohols, esters, ketones and aldehydes, mixtures thereof, and mixtures thereof containing water. Preferred solvents for Solvent A include methanol, ethanol, propanol, isopropanol, and acetone. In one preferred embodiment the Solvent A is 90% (i.e., 180 proof) aqueous ethanol. Algae may be extracted according to Extraction Protocol A at ambient temperature, or preferably near the boiling point of Solvent A. Extraction Protocol A includes contacting the algae with the Solvent A for a period of time sufficient to effect solubilization of the MGDG-EPA lipids from the algae. For example, a presently preferred extraction with 90% aqueous ethanol is accomplished at a temperature near the boiling point within 20 minutes. The status of Extraction Protocol A may be monitored by a variety of techniques, e.g., HPLC as in FIG. 1, TLC as in FIG. 2, GC and the like. Upon cooling the mixture, e.g., the ethanolic extract containing MGDG-EPA, may be separated from the residual algal solids by filtration to yield the "extraction solvent extract" (i.e., herein after referred to as "Extract A").

"Extract A" (above) is next fractionated by phase separation using a "first solvent purification protocol" (i.e., hereinafter referred to as "Purification Protocol B") using an "organic water-immiscible solvent" and water (i.e., Solvent B). Solvent B selectively solubilizes the MGDG-EPA lipids present in Extract A. The water in solvent B serves to remove highly polar components, e.g., sugars, amino acids, and other water soluble components. Suitable solvents for inclusion in Solvent B include non-polar organic solvents such as hydrocarbons, ethers, and chlorinated hydrocarbons among others. Preferred solvents for inclusion in Solvent B include pentane, hexane, heptane, petroleum ethers, diethyl ether, dichloromethane and chloroform among others. In one preferred embodiment, Solvent B is hexane and water. After thorough agitation of Extract A with Solvent B the aqueous phase is separated from the organic phase, which is recovered, i.e., Extract B. Removal of the organic solvents from Extract B yields a crude algal lipid extract containing MGDG-EPA. In one presently preferred embodiment of Purification Protocol B, the solvent system is a mixture of ethanol, hexane and water in a ratio of 1:1:1.

"Extract B" (above) is next fractionated by polar chromatography (i.e., Purification Protocol C). A solution of Extract B is prepared in a suitable solvent, e.g., 10% ethanol in hexane, and the solution is applied to a polar chromatographic column. Suitable solid phases for use in Purification Protocol C include e.g., alumina, deactivated alumina, silicic acid, silica gel, DEAE cellulose, and other polar solid phases. In a presently preferred embodiment, the polar solid phase is deactivated alumina (i.e., described in Example 1, below). In Purification Protocol C, Extract B is fractionated by polar chromatography using one or more "fractionating solvents" (i.e., referred to hereinafter as the "Solvents C"). Solvents C may be comprised of mixtures of suitable solvents in varying ratios, including water and mixtures of polar and non-polar organic solvents. Suitable polar organic solvents for inclusion in Solvents C include alcohols, esters, ethers, ketones, and aldehydes among others. Presently preferred polar organic solvents for inclusion in Solvents C include alcohols and esters such as methanol, ethanol, and ethyl acetate. Preferred non-polar organic solvents for inclusion in Solvents C include pentane, hexane, diethyl ether, dichloromethane, and chloroform. In one preferred embodiment, a Solvent C comprises ethanol, hexane and water in a mixture. Polar chromatography is accomplished according to Purification Protocol C by running the Extract B solution onto the column under conditions suitable for adsorption of MGDG-EPA lipids onto the column matrix. Components are then sequentially stepwise eluted from the column matrix using increasingly polar solvents or solvent mixtures, i.e., the Solvents C. In one preferred method according to Purification Protocol C the Extract B lipids adsorbed to a polar column of deactivated alumina are stepwise eluted using: (i) Solvent C1, 10% ethanol in hexane; (ii) Solvent C2, 40% ethanol in hexane; (iii) Solvent C3, 100% ethanol; and (iv) Solvent C4, 20% water in ethanol. According to the latter preferred method, Solvent C4, (i.e., 20% water in ethanol), contains an enriched MGDG-EPA fraction hereinafter referred to as "Fraction A".

"Fraction A" (above) may be further separated using non-polar chromatography (i.e., referred to hereinafter as Purification Protocol D) to yield a further enriched MGDG-EPA fraction (i.e., "Fraction B"). In particular, Fraction A is first dried and then resuspended in a suitable solvent such as ethanol/water (1:1). The solubilized Fraction A is applied to a non-polar chromatographic column. Suitable non-polar solid phases for use in Purification Protocol D include any non-polar or reverse phase solid phase. A presently preferred solid phase for use in Purification Protocol D is reverse phase silica, and a presently most preferred solid phase is reverse phase octadecylsilyl silica (ODS). According to Purification Protocol D, further enrichment of MGDG-EPA from Fraction A is accomplished by elution with non-polar chromatography using one or more "fractionating solvents" (i.e., referred to hereinafter as the "Solvents D"). Solvents D may be comprised of mixtures of suitable solvents in varying ratios, including water and mixtures of polar organic solvents. Suitable polar organic solvents for inclusion in Solvents D include alcohols, esters, ethers, ketones, and aldehydes among others. Preferred polar organic solvents for inclusion in Solvents D include alcohols and esters such as methanol, ethanol, and ethyl acetate. In one preferred embodiment, a preferred Solvents D includes ethanol and water mixed in varying ratios in the different respective Solvents D. Non-polar chromatography is accomplished according to Protocol D by running a solution of Fraction A onto the column under conditions suitable for adsorption of MGDG-EPA lipids onto the column matrix. Components are then sequentially stepwise eluted from the column matrix using decreasingly polar solvents or solvent mixtures, i.e., the Solvents D. In one preferred method according to Protocol D the Fraction A lipids adsorbed to a non-polar column of ODS are stepwise eluted using: (i) Solvent D 1, 50% aqueous ethanol (100 proof); (ii) Solvent D2, 70% aqueous ethanol (140 proof); (iii) Solvent D3, 90% aqueous ethanol (180 proof); and (iv) Solvent D4, 100% aqueous ethanol (200 proof). According to the latter preferred method, Solvent D3, (i.e., 90% ethanol), contains the MGDG-EPA fraction hereinafter referred to as Fraction B.

In an alternative embodiment, "Fraction A" (Purification Protocol C, above; from polar chromatography) may be subject to an additional step of polar chromatography (i.e., Purification Protocol E). A solution of Fraction A is prepared in a suitable solvent, e.g., 10% ethanol in hexane, and the solution is applied to a polar chromatographic column. Suitable solid phases for use in Purification Protocol E include e.g., silicic acid, silica gel, DEAE cellulose, an other polar solid phases. In a presently preferred embodiment, the polar solid phase is silicic acid (i.e., described in Example 1, below). In Purification Protocol E, Fraction A is further fractionated by polar chromatography using one or more "fractionating solvents" (i.e., referred to hereinafter as the "Solvents E"). Solvents E may be comprised of mixtures of suitable solvents in varying ratios, including mixtures of polar and non-polar organic solvents. Suitable polar organic solvents for inclusion in Solvents E include alcohols, esters, ethers, ketones, and aldehydes among others. Presently preferred polar organic solvents for inclusion in Solvents E include alcohols and esters such as methanol, ethanol, and ethyl acetate. Preferred non-polar organic solvents for inclusion in Solvents E include pentane, hexane, diethyl ether, dichloromethane, and chloroform. In one preferred embodiment, a Solvent E comprises ethanol and hexane in a mixture. Polar chromatography is accomplished, according to Purification Protocol E, by running the Fraction A solution onto the column under conditions suitable for adsorption of MGDG-EPA lipids onto the column matrix. Components are then sequentially stepwise eluted from the column matrix using increasingly polar solvents or solvent mixtures, i.e., the Solvents E. In one preferred method according to Purification Protocol E, the Fraction A lipids adsorbed to a polar column of activated silicic acid are stepwise eluted using: (i) Solvent E1, 10% ethanol in hexane; (ii) Solvent E2, 20% ethanol in hexane; (iii) Solvent E3, 40% ethanol in hexane; (iv) Solvent E4, 60% ethanol in hexane, and (v) Solvent E5 100% ethanol. According to the latter preferred method, Solvent E2, (i.e., 20% ethanol in hexane), contains an enriched MGDG-EPA fraction hereinafter referred to as Fraction C.

Fractions B and C, above, are illustrative compositions of the subject "MGDG-EPA containing microalgal lipid preparation" of the invention.

In still other embodiments the invention provides DGTS compositions useful for promoting inflammation and for promoting biological activities triggered by protein kinase C. The ability of purified DGTS microalgal lipid preparations to potentiate phorbol ester-induced inflammation is recognized to have importance as follows: namely, the active principle in croton oil inducing inflammation is reported to be the phorbol diester 12-O-tetradecanoylphorbol-13-acetate (TPA). According to Guftason et al. (J. Med. Chem. 35: 1978, 1986) TPA and phorbol monoester "prostratin" show cytoprotective activity against HIV, and these authors suggest that protein kinase C (PKC) isozyme activation may be a common pathway for mediating these effects. It is conceivable that membrane changes induced by PKC activation do not favor retroviral entry, early post-entry events, or viral encapsidation and budding from the cell. Prostratin reportedly lacks the tumor promoting activity of TPA, and might be useful as an non-toxic phorbol inducer of PKC. Interestingly, DGTS has certain structural similarities to phosphatidylserine (i.e., the diacylglycerol backbone, carboxyl residue, and amino residue). Phosphatidylserine is reported to play an important role in PKC activation. It is considered likely that the highly unsaturated EPA fatty acid moieties of DGTS may promote the action of TPA on PKC by serving as an 'improved' phosphatidyl serine activator of PKC activity.

The following examples are offered by way of illustration, not limitation.

EXAMPLE 1

This example illustrates two different preparations (Preparations I and II) of an MGDG-EPA containing ricroalgal lipid preparation according to the instant invention.

Preparation Ia: The marine microalga *Chlorella minutissima* was grown in cultivation tanks 4'×10' with a paddle wheel system for agitation and a culture medium depth of 10"–12". The culture medium consisted of sea water, supplemented with ammonium nitrate (8 mM), sodium bicarbonate (5 mM), potassium dihydrogen phosphate (0.04 mM), and iron versenate (0.02 mM). The cultures were grown in full sunlight, or in plastic covered green houses, and the nutrient levels were measured weekly and additional nutrients added as required. When the cultures reached an optical density of 1.0 (measured at 690 nm) the algae were harvested. Fifty percent of each of 6 culture tanks was harvested giving a total of approximately 700 gallons.

The culture was pumped through a mixing tower where metered amounts of coagulant (Calgon WT-25 11) were added with rapid agitation. The mixture next passed into a non-stirred column where metered amounts of flocculent (Betz Polymer 1160) were added, and thence into settling tanks. Settling was rapid and a large proportion of supernatant water was discarded. After further settling overnight, in excess of about 90% of the supernatant liquid was discarded, leaving a total volume of approximately 25 gallons. To this was added 3.64 kg of diatomaceous earth (DE) as a filter aid. Further rapid settling occurred, thus allowing the removal of more supernatant water to leave 12 gallons of slurry. The slurry was vacuum filtered to yield a cake weighting 11.4 kg. The dry weight of algae contained in the cake was 686 gm.

The algal cake was extracted in 1.5 kg aliquots by adding to 4 L of boiling 90 percent aqueous ethanol, bringing the mixture back to a boil (5–10 minutes), and then continuing boiling for 10 minutes. The extract was obtained by filtration through a Buchner funnel under vacuum to remove solids. Water and hexane were added to the cooled extract to provide a final proportion (extract/hexane/water) of 1:1:1 and the mixture was agitated well and allowed to separate into two phases. The lower, aqueous ethanol phase contained water soluble materials, including sugars, amino acids, and some pigments. The upper hexane phase contained the crude lipid extract. The solvent was evaporated from the upper phase and the residue taken up in a minimal amount of 10% ethanol in hexane. At this stage small aliquots were taken for determination of dry weight, for thin-layer chromatography, and for fatty acid analysis by trans-esterification and gas chromatography. Total lipid extract was 98.8 gm, or 14.4% of the dry weight of the algae. The raw extract contained on average about 25% (w) MGDG-EPA, 25% (w) DGTS, 25% (w) pigments and other neutral lipids, and 25% (w) DGDG with phospholipids. A summary of the relative ratios of MGDG-EPA to DGTS in 8 different batch extracts is presented in TABLE 1, below.

TABLE 1

Relative Proportions of MGDG—EPA and DGTS in Eight Different Microalgal Raw Extracts Prepared From Algae Grown In the Range of 8° C. to 16° C.

| Extract # | MGDG—EPA | DGTS | Purification Ratio: MDGD—EPA/DGTS |
|---|---|---|---|
| 1 | 65 | 35 | 1.86 |
| 2 | 75 | 25 | 3.0 |
| 3 | 28 | 72 | 0.39 |
| 4 | 55 | 45 | 1.22 |
| 5 | 30 | 70 | 0.43 |
| 6 | 66 | 44 | 1.5 |
| 7 | 18 | 82 | 0.22 |
| 8 | 76 | 24 | 3.17 |
| Mean ± S.D. | 52 ± 21 | 50 ± 21 | 1.48 ± 1.1 |

The ratio of MGDG-EPA to DGTS-EPA was highly variable at this stage of purification, but on average there were approximately equal amounts of each lipid in the extra.

The crude lipid exract was dissolved in 10% ethanol in hexane to a total volume of 880 ml, applied to a 4"×24" alumina column prepared as follows: namely, activated alumina (aluminum oxide) of a chromatographic grade (Aldrich Chemical Co., Brockman grade I, acidic, about 150 mesh) was deactivated by suspendind it overnight in two volume of aqueous ethanol at a mixture of 70 parts ethyl alcohol to 30 part water. The deactivated alumina was then packed into the column as a hurry in the water/alcohol mixture. The column was washed well with four volumes of absolute ethanol to remove the water, followed by a wash with one column volume of 40% ethanol in hexane and two column volumes of 10% ethanol in hexane.

The crude lipid extract (880 ml) was pumped onto the alumina column and eluted with 4 L of 10% ethanol in hexane, 3 L of 40% ethanol in hexane, 4 L of 100% ethanol, 4 L of 20% water/80% ethanol and 3 L of an ethanol wash. All fractions were vacuum evaporated to dryness and the residues taken up in 10% ethanol in hexane. Samples of the fractions were applied to TLC plates for analysis of lipid composition.

The 20% water/80% ethanol fraction, which contained the majority of the MGDG-EPA (i.e., by weight) was evaporated to dryness (weight 12.4 gm) and taken up in ethanol/water 1:1. The MGDG-enriched fraction was then further separated in one embodiment using a reverse-phase ODS column.

Separation of the MGDG-enriched fraction on the reverse-phase ODS column 2"×12" (Preparative C18, 125A, Millipore Corp.) was accomplished as follows: namely, the ODS-silica was slurried with absolute ethanol and packed in the column in ethanol. After a wash with 1 L of absolute ethanol, the column was washed with 1 L of 75% ethanol/ 25% water, then 1.5 L of ethanol/water 1:1. The MGDG-EPA containing fraction from the alumina column was divided in two, and one portion (about 6.2 gm) at a time separated on the ODS column in two separate runs. Elution was accomplished with 1 L of 50% aqueous ethanol, 1 L of 70% (140 proof) aqueous ethanol, 1.5 L of 80% (160 proof) aqueous ethanol, 1 L of 85% (170 proof) aqueous ethanol, 1.5 L of 90% (180 proof) aqueous ethanol and 2.5 L of absolute ethanol. In each run, the 90% aqueous ethanol fraction contained the bulk of the MGDG-EPA (approx. 90% of the total) as determined by TLC. These 90% fractions from the two runs were combined and evaporated (total weight 10.2 gm). The composition of the combined fractions was approximately 60% MGDG-EPA, 7% DGDG, and 3% PC (with minor components of carotenoids and chlorophyll). The remaining 30% was diacylglyceryl-N,N,N-trimethylhomoserine ("DGT S-EPA").

Preparation Ib:

A process similar to that described above for Preparation Ia was employed, using the solvent systems of Preparation Ia but substituting two columns, i.e., a 2" diameter alumina column and a 44 mm diameter ODS column, for the larger columns of Preparation Ia. In Preparation Ib the 90% ethanol in $H_2O$ fraction yielded a lipid preparation that was approximately 60% MGDG-EPA, 10% DGTS-EPA, 20% DGDG and 10% phospholipids with traces of pigments (purification ratio=6.0 MGDG-EPA/DGTS).

Preparation II: A second preparation according to the method disclosed above yielded the following result summarized in TABLE 2, below.

TABLE 2

Percentage Composition of Lipids in Fractions During Preparation of a Microalgal Lipid Preparation: Alumina Chromatography

| Eluate | Description of Fraction | MGDG—EPA % | DGDG/PL % | Pigments % | DGTS % | Purification Ratio: MGDG—EPA/DGTS |
|---|---|---|---|---|---|---|
| 0 | raw-extract | 25 | 25 | 25 | 25 | 1.0 |
| 2 | 40% EtOH/hexane | 10 | — | 30 | 60 | 0.17 |
| 3 | 100% EtOH | — | 30 | 10 | 60 | — |
| 4 | 20% $H_2O$/EtOH | 50 | 20 | 15 | 15 | 3.33 |
| 5 | EtOH wash | 50 | 20 | 15 | 15 | 3.33 |

In animal experiments (EXAMPLES, below), reducing the level of DGTS in the microalgal lipid preparation was determined to be a key element to producing an anti-inflammatory composition, since DGTS was capable of promoting inflammation and masking the anti-inflammatory effects of MGDG-EPA.

Figure 2:
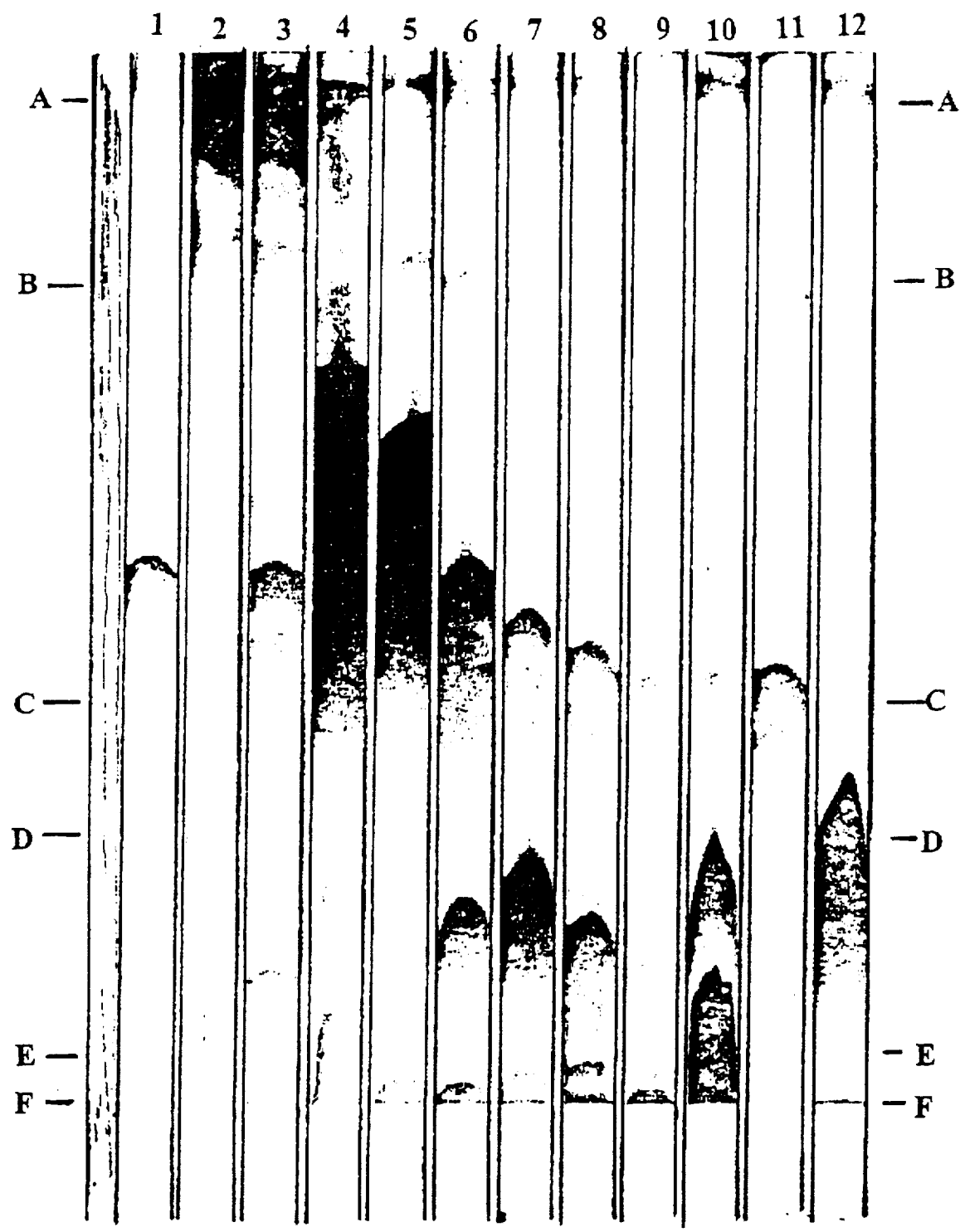
FIG. 2 depicts a thin layer chromatogram of fractions from silicic acid column chromatography, including a representative microalgal lipid preparation according to the invention, in this case the preparation identified as fraction 20-III (see the HPLC chromatogram of FIG. 1), this fraction had greater than 95% by weight of MGDG-EPA and less than about 5% of contaminants including diacylglyceryl-N, N,N-trimethylhomoserine (structure III), chlorophylls, carotenoid and phospholipids (i.e., phosphatidyl serine, phosphatidyl ethanolamine and phosphatidyl choline.) Visualization of all organic compounds in fractions 20-III on the TLC was by the method of sulfuric acid charring.

Further purification of the MGDG-enriched fraction (17 g) on activated silicic acid was accomplished as follows: namely, silicic acid was activated and regenerated by baking the packing in an oven at 1750° F. After cooling, the silicic acid was made slurried with absolute ethanol and poured into a 4"×12" glass column. The column bed was washed with 40% ethanol in hexane and then equilibrated with 10% ethanol in hexane. The MGDG-EPA containing fractions from the alumina column were evaporated, dissolved in 10% ethanol in hexane, and pumped onto the silicic acid column. Elution was accomplished with 2 L of 10% ethanol in hexane, 3 L of 20% ethanol in hexane, 2 L of 40% ethanol in hexane, 2 L of 60% ethanol in hexane, followed by 2 L of absolute ethanol. The 20% elution was collected in 3 sequential fractions, and the 40% elution was collected in two sequential fractions. The 20% ethanol/hexane fraction contained the bulk of the MGDG-EPA (approx. 80% of the total; 10.7 gm) as determined by TLC (FIG. 2). Fractions 20-II and 20-III are representative of the microalgal lipid preparation of the instant invention. The pigments were removed in the 10% fraction and DGTS (along with DGDG and phospholipids) were collected primarily in the 40% and 60% fractions. Quantification of the components of the fractions was achieved by TLC and HPLC. The results of an illustrative silicic acid chromatographic purification are presented in TABLE 3, below.

TABLE 3

Percentage Composition of Lipids in Fractions During Preparation of a Microalgal Lipid Preparation: Silicic Acid Chromatography

| Eluate | Description of Fraction | MGDG—EPA % | DGDG/PL % | Pigments % | DGTS % | Purification Ratio: MGDG—EPA/DGTS |
|---|---|---|---|---|---|---|
| 0 | 20% H$_2$O/EtOH fraction from Alumina | 50 | 20 | 15 | 15 | 3.33 |
| 1 | 10% EtOH/hexane | — | — | 98 | 2 | — |
| 2 | 20%-I | 35.3 | 10.9 | 8 | 45.8 | 0.77 |
|   | 20%-II | 95.7 |  | 2 | 2.3 | 41.61 |
|   | 20%-III | 95.3 |  | 1.9 | 2.8 | 34.04 |
| 3 | 40%-I | 60.3 | — | — | 33.4 | 1.81 |
|   | 40%-II | 30 | 5 | 5 | 60 | 0.5 |
| 4 | 60% | 30 | 5 | 5 | 60 | 0.5 |

The purification ratio (% MGDG-EPA/% DGTS) at this stage was about in the range of 34–42, depending upon the fraction. A representative sampling of the composition of 6 different lots prepared according to the methods of Preparations f r is shown in TABLE 4, below.

TABLE 4

Microalgal Lipid Preparations Produced by Alumina and Silicic Acid Chromatography: MGDG—EPA Purity

| Lot # | MGDG—EPA % w | DGTS % w | Purification Ratio: MGDG—EPA/DGTS |
|---|---|---|---|
| 1 | 95.5 | 1.5 | 63.7 |
| 2 | 89.1 | 6.6 | 13.5 |
| 3 | 93.8 | 5.5 | 17.1 |
| 4 | 96.8 | 2.6 | 37.2 |
| 5 | 95.7 | 2.3 | 41.6 |
| 6 | 97.0 | 2.1 | 46.2 |

EXAMPLE 2

This Example illustrates the characterization of the MGDG-EPA components of Example 1.

A sample containing MGDG-EPA from EXAMPLE 1 was subjected to separation by preparative thin layer chromatography. Two major components were isolated, namely, MGDG-EPA and DGTS-EPA. Each component was removed from the plate by scraping and eluted from the silica gel. The proton NM R spectra of the MGDG-EPA component is presented in FIG. 3. In addition, a portion of each component (i.e., MGDG-EPA and DGTS-EPA) was trans-esterified and the resulting fatty acid esters were analyzed by gas chromatography. The identity of the components of the fatty acid ester mixtures was determined by comparing the retention times with known standards that were run in the column immediately prior to the unknown components. Carbon number plotting was also used to verify the identity of the fatty acids. The fatty acids of the MGDG-EPA components are (in percent by weight) presented in TABLE 5, below.

TABLE 5

Fatty Acids in the MGDG—EPA Containing Microalgal Lipid Preparation

| Fatty Acid | Percent* |
|---|---|
| 12:0 | trace |
| 14:0 | 5.4 |
| 16:0 | 0.2 |
| 16:1 | 1.4 |
| 20:4 | 1.5 |
| 20:5 | 91.5 |

*percent by weight.

In TABLE 5, above, the first number of the fatty acid represents the number of carbon atoms in the fatty acid, and the number following the colon represents the number of double bonds in the hydrocarbon chain of the fatty acid. The identity of the major fatty acid constituent (i.e., 20:5) as eicosapentaenoic acid was confirmed by mass spectrometry. Mass spectrometry was also used in elucidating the structure of MGDG-EPA and DGTS-EPA. In one sample of purified DGTS that was analyzed by the same methods, EPA represented 93% (w) of the acylated fatty acids present in the compound.

EXAMPLE 3

This EXAMPLE illustrates the efficacy of the composition of the instant invention as an anti-inflammatory agent as determined in a mouse ear swelling test.

Kinetics: To determine the kinetics of ear swelling (and reduction in swelling), both ears of mice were treated with either an aqueous gel (see Materials and Methods, below) or a formulation of gel and an MGDG-EPA-containing microalgal lipid preparation made up, in this example of about 85% by weight of MGDG-EPA, 15% by weight DGTS, and trace chlorophylls. EPA content in this particular MGDG-EPA preparation was 80–90% of the fatty acids present in the total preparation. An anti-inflammatory gel was formulated (Materials and Methods, below) consisting of 0.5% of the MGDG-EPA containing microalgal lipid preparation and 99.5% by weight gel. Treatments involved the application to a mouse ear of 5 mg of either gel (control) or the 0.5% MGDG-EPA containing gel (test), according to the Methods indicated following EXAMPLE 8, below. Five mice (i.e., 10 ears) were used for each control or test group. Two hours after the last application, 10 µl of a 10% croton oil solution in acetone was applied to each ear to induce inflammation. Measurements were taken before treatment, immediately before croton oil challenge (t=0), and at 8, 24 and 48 hours after the croton oil application. For comparative purposes the experiment included the anti-inflammatory corticosteroid composition 0.05% betamethasone dipropionate. The results of the experiment are presented in TABLE 6, below, with ear thickness in microns.

TABLE 6

Kinetics of Ear Swelling and Reduction in Ear Swelling ($\mu \pm$ S.E.) with MGDG—EPA

| Time (hr.)[a] | Gel Control | Test Formulation | % Reduction in Swelling[b] |
|---|---|---|---|
| | | MGDG—EPA (0.5%) | |
| 0 | 115 ± 17 | 48 ± 13* | 57 |
| 8 | 169 ± 22 | 161 ± 17 | 6 |
| 24 | 207 ± 26 | 129 ± 15* | 37 |
| 48 | 184 ± 11 | 119 ± 9* | 34 |
| | | betamethasone dipropionate (0.05%) | |
| 8 | — | −7 ± 6 | 100 |
| 24 | — | 191 ± 18 | 8 |

*statistically significant at the p < 0.05 level, Wilcoxon Rank Sum Test;
[a]Time in hours after induction of ear swelling with croton oil;
[b]% reduction in swelling = [Mean Gel Control] − [Test Formulation] / [Mean Gel Control] × 100%.

The results presented in TABLE 6 show the following properties of this inflammation model: namely, (a) daily topical application of gel induced approximately a 48% increase in ear thickness in the control group prior to induction of ear swelling with croton oil (i.e., 0 hr. Gel Control, baseline ear thickness in the Gel-only group was 238μ); (b) daily topical treatments with gel containing the MGDG-EPA composition reduced the non-specific swelling (i.e., 0 hr. Test Formulation); (c) croton oil induced an 87% increase in ear thickness in the Gel-only controls with maximal swelling occurring at about 24 hours; and, (d) the anti-inflammatory effects observed at 24 hr. with MGDG-EPA treatment were better than those recorded using 0.05% betamethasone dipropionate treatments. Treatments with the test formulation containing MGDG-EPA induced a statistically significant reduction in ear swelling at the 24 hr. and 48 hr. time points, when compared with the gel-treated control. Reduction in ear swelling was approximately 34–37% at this 0.5% dose level of MGDG-EPA microalgal lipid preparation.

Dose-Response: The dose response characteristics of the MGDG-EPA microalgal lipid preparation used in TABLE 5 (above) were determined using the 24 hr. time point after induction of swelling with croton oil. Treatments with test or control (gel) formulations were according to the 5 day pretreatment regimen used in the kinetic studies above.

TABLE 7

Dose-Response Reduction in Ear Swelling ($\mu \pm$ S.E.) with Different MGDG—EPA Dosage Forms

| Dose[a] | t = 0 hr. | t = 24 hr. | % Reduction in Swelling[b] |
|---|---|---|---|
| 0 | 115 ± 17 | 207 ± 26 | 0 |
| 0.5 | 48 ± 13* | 129 ± 15* | 38 |
| 1.0 | 68 ± 12 | 158 ± 15 | 24 |
| 3.0 | 64 ± 13 | 176 ± 17 | 15 |
| 5.0 | 145 ± 28 | 251 ± 15 | −21 |

*statistically significant at the p < 0.05 level, t-Test;
[a]Dose = weight percent of the MGDG—EPA microalgal lipid preparation in gel;
[b]% reduction in swelling = [Mean 0 Dose] − [Mean Test Dose] / [Mean 0 Dose] × 100% for the 24 hr. observation point.

The results presented in TABLE 7 show that prophylactic treatments with the topical compositions formulated with lower doses of (0.5%) of this particular microalgal lipid preparation were more effective than higher doses (i.e., 5.0%) in reducing croton oil-induced swelling.

EXAMPLE 4

Comparative Anti-Inflammatory Activity of Different Fatty Acyl-Glycerides with Different Polar Head Groups Structure-Function Studies: The relative participation of the different moieties comprising the MGDG-EPA molecule were evaluated by comparing the anti-inflammatory activities of different purified lipid formulations in croton oil-induced ear swelling. A description of the different lipids used in these studies appears in the Materials and Methods section, immediately following EXAMPLE 8, below. The croton oil-induced mouse ear swelling model was conducted in the manner described in EXAMPLE 3, above. However, in this case the algal lipid preparation was made of 95% MGDG-EPA, 3% DGTS and 2% of chlorophyll and xanthophyll pigments. The test compositions identified in TABLE 8 below were used to formulate topical compositions having either 0.5% (w) or 2.0% (w) of the test composition in a carbopol-based gel carrier (see Materials and Methods, below). The compositions were applied to the ears of Balb/c mice twice a day for five days. Ear swelling was measured 24 hours after inducing inflammation by topical administration of 10% croton oil in acetone. The results are summarized in TABLE 8, below.

TABLE 8

Ear Swelling ($\mu +$ S.D.): 24 hr. After Croton Oil Induced Inflammation

| Grp. No. | Test Composition | Fatty acid Type | Fatty acid (%) | Percent by Weight of Preparation in Composition 0.0 | 0.5 | 2.0 |
|---|---|---|---|---|---|---|
| 1 | Negative Control | none | none | 266 ± 76.0 | — | — |
| 2 | Non-Treated Control | none | none | 322 ± 26.2 | — | — |
| 3 | MGDG—EPA | 20:5 | 83[b] | — | 187 ± 65.5*† | 162 ± 25.3*† |
| 4 | MGDG—palmitolenic | 16:3 | 25[b] | | | |
| | | 18:3 | 75[b] | — | 221 ± 62.3 | 201 ± 68.4 |
| 5 | EPA ethyl ester | 20:5 | 93[c] | — | 277 ± 66.2 | 221 ± 53.8 |
| 6 | Fish oil | 22:6 | 24[c] | — | 280 ± 68.3 | 246 ± 50.6 |
| | | 20:5 | 36[c] | | | |

TABLE 8-continued

Ear Swelling ($\mu$ + S.D.): 24 hr. After Croton Oil Induced Inflammation

| Grp. Test | Fatty acid | | Percent by Weight of Preparation in Composition | | |
|---|---|---|---|---|---|
| No. Composition | Type | (%) | 0.0 | 0.5 | 2.0 |

*Negative control, vehicle; Non-treated control, only croton oil induced inflammation with no treatment; lipids are described in the Materials and Methods section immediately following EXAMPLE 8, below;
<sup>b</sup>percentage of the respective fatty acids out of the total present in the preparation;
<sup>c</sup>% of total weight of the lipid preparation;
*, statistically significant at the p < 0.05 level (Student's t-test) in comparison with the values recorded in Group 1;
†, statistically significant at the p < 0.05 level (Student's t-test) in comparison with the values recorded in Group 2.

The results presented in TABLE 8 show that reduction of ear swelling by MGDG-EPA in this assay required both the galactosyl moiety (i.e. EPA ethyl ester and Fish oil were inactive and 20% EPA-ethyl ester in petrolatum was shown to potentiate inflammation, data not include in the TABLE) and the eicosapentaenoyl moiety (i.e., MGDG-palmitolenic acid from spinach was inactive), i.e., the entire MGDG-EPA molecule was required in order to obtain anti-inflammatory activity within the dose range tested. Further, when the values recorded with MGDG-EPA and those recorded in Groups 5 or 6 were compared, the difference was statistically significant (p<0.05).

Phosphatidyl ethanolamine (PE)/phosphatidyl glycerol (PG)-EPA is a 90% pure mixture of PE and PG in which approximately 53% of the fatty acid moieties are made of EPA. Groups of 3 mice were treated with 16% PE/PG-EPA or 10% PE-AA in petrolatum according to the protocol described in EXAMPLE 3, above. The results are presented in TABLE 9, below.

TABLE 9

Kinetics of Croton Oil-Induced Ear Swelling Measured as Ear Thickness ($\mu$ ± S.E.; n = 6 ears) and Weight of Biopsy (mg ± S.E.)

| | Time (hrs.) | Petrolatum Control | PE/ PG—EPA | PE—AA |
|---|---|---|---|---|
| Swelling ($\mu$) | 8 | 260 ± 17 | 135 ± 10* | 140 ± 14* |
| | 24 | 292 ± 18 | 163 ± 25* | 222 ± 25* |
| | 48 | 282 ± 19 | 197 ± 15* | 210 ± 17* |
| Biopsy Weight (mg) | 48 | 3.17 ± 0.21 | 2.47 ± 0.19 | 2.52 ± 0.10 |

*Statistically significant (p < 0.05) in comparison with the petrolatum-control; Wilcoxon Rank Sum Test.

The data in TABLE 9 show that phospholipids acylated with EPA or AA, when applied topically, exhibit anti-inflammatory activity. These data are inconsistent with a substrate-substitution hypothesis, since AA is a substrate for arachidonic acid metabolism, and if anything, according to the hypothesis, it should potentiate inflammation.

In a separate experiment, 2% PE/PG-EPA (instead of the 10% and 16% used above) in petrolatum was observed to induce a time-dependent potentiation of croton oil-induced ear swelling; at 8 hrs. the composition inhibited but at 24 hrs. it potentiated (TABLE 10, below). By comparison, the 2% MGDG-EPA composition used in this experiment was uniformly anti-inflammatory.

TABLE 10

Kinetics of Croton Oil-Induced Ear Swelling: Ear Thickness ($\mu$ ± S.E.)

| | Time (hrs.) | Petrolatum Control | 2% PE/ PG—EPA | 2% MGDG—EPA |
|---|---|---|---|---|
| Swelling ($\mu$) | 0 | −12 ± 4.9 | 56 ± 5.8* | 14 ± 7.5* |
| | 8 | 152 ± 10.6 | 99 ± 20.8* | 85 ± 19.3* |
| | 24 | 109 ± 17.5 | 189 ± 19.2* | 67 ± 11.6* |

*Statistically significant difference (p < 0.05) in comparison with the petrolatum-control.

The combined results presented in TABLES 8–10, above, suggest that topical anti-inflammatory activity may be achieved with a substituted glycerol containing a proper polar head group and fatty acids of sufficient carbon chain length and degree of unsaturation. The apparent requirement for a polar head group is consistent with a membrane-integration hypothesis of MGDG-EPA action. The increased efficacy of the galactolipid, i.e., in comparison with the phospholipid, is also consistent with the latter hypothesis. The importance of the species of head group is further underscored by the results presented in EXAMPLE 5, below.

Levels of MGDG-EPA in Treated Skin Samples: The existence of a cellular pool of available EPA substrates is an implicit feature of a substrate-substitution hypothesis. Were MGDG-EPA to exert its anti-inflammatory effects in this manner, then, the cellular pool size of EPA would seemingly need to be large, or at least more readily available than AA. Experiments were performed to test this hypothesis by measuring EPA content in mouse skin treated with MGDG-EPA containing microalgal lipid preparations.

Fatty analysis was performed by gas chromatography on excised biopsy samples of epidermis of three untreated mice, three mice treated daily for 26 weeks with petrolatum, and three mice treated daily for 7 weeks with 5% MGDG-EPA in petrolatum followed by 19 week's treatment with 1% MGDG-EPA in petrolatum. Normal mouse epidermis was found to contain low, barely detectable levels of EPA.

The results for 5 of 29 fatty acids detected are presented in TABLE 11, below.

TABLE 11

Percent Composition of Total Fatty Acids in Skin of Mice Treated with MGDG—EPA Containing Microalgal Lipid Preparations

| Sample No. | Treatment | Selected Fatty Acid Composition (%) | | | | |
|---|---|---|---|---|---|---|
| | | 16:0 | 18:2n6 | 18:1n9 | 20:4n6 | 20:5n3 |
| 1 | Petrolatum- | 15.27 | 23.51 | 15.35 | 6.49 | 0.50 |
| 2 | base | 13.28 | 30.67 | 27.25 | 2.73 | 0.35 |
| 3 | | 12.88 | 29.82 | 26.09 | 2.67 | 0.48 |
| 4 | MGDG—EPA | 12.01 | 26.88 | 24.13 | 3.48 | 0.49 |
| 5 | | 12.63 | 32.28 | 27.54 | 1.84 | 0.25 |
| 6 | | 10.55 | 31.34 | 29.77 | 2.13 | 0.45 |

The results presented in TABLE 11 show that there is little, if any, difference between the fatty acid composition of skin treated with petrolatum-base or with MGDG-EPA containing microalgal lipid preparation. On average, there was about 6-times more arachidonic acid (20:4) in the skin samples than EPA (20:5).

The results obtained in this experiment are not in agreement with a simple hypothetical model of MGDG-EPA inhibition of inflammation by substrate substitution.

EXAMPLE 5

Biological Activities of Contaminating Polar Lipids

DGTS-EPA: DGTS-EPA was identified as a contaminant that is present in impure microalgal lipid preparations and is synthesized by microalgae (EXAMPLE 1, above). DGTS-EPA was further purified to approximately 98% and then tested to determine its biological activity by formulating a 2% topical composition in petrolatum (i.e., according to the methods described in EXAMPLES 3 and 4, above). Prophylactic treatments were administered over 5 days and croton oil-induced inflammation was induced on day 5 and ear measurements were taken at 24 hr. thereafter (i.e., methods according to EXAMPLES 3 and 4, above). The petrolatum base of the vehicle was used as a negative control. In the same experiment a lipid preparation made up of approximately 50% DGTS-EPA, 30% MGDG-EPA, 20% DGDG and phospholipid-EPA was tested at a concentration of 2% in petrolatum. The results recorded in this study are summarized in TABLE 12, below.

TABLE 12

DGTS—EPA Potentiates Ear Swelling (µ ± S.D.) Induced by Croton Oil: All Algal Lipid Preparations Were Tested at 2% in Petrolatum

| Grp. | Test Composition | |
|---|---|---|
| 1 | Petrolatum | 109 ± 55.5 |
| 2 | 98% DGTS—EPA | 341 ± 93.6* |
| 3 | 30% MGDG—EPA mixture with 50% DGTS—EPA | 175 ± 78.1* |

*Statistically significant (p < 0.05) in comparison with the petrolatum (vehicle)-only control; t-Test.

The results presented in TABLE 12 show that highly purified DGTS-EPA has a very marked ability to promote inflammation induced by croton oil (i.e., over a 3.1-fold increase in inflammation relative to the petrolatum control). Inclusion of DGTS as a contaminant/impurity in an MGDG-EPA composition (group 3) nullified the anti-inflammatory activity resident in MGDG-EPA, even when the DGTS concentration in the gel composition was only 1%.

EXAMPLE 6

Studies of Mechanism: Histology of MGDG-EPA Treated and Control Mouse Tissues Following Croton-Oil-Induced Inflammation It has been proposed previously that EPA inhibits production of arachidonic acid metabolites which are inflammatory mediators. While prostaglandins and prostacyclin production by neutrophils seem to play a role in perpetuating an ongoing inflammatory response, i.e., a response that has already been triggered, the early events involved in triggering an inflammatory response are less well understood. A number of candidate mediators may be involved in triggering inflammatory responses in tissues, e.g., plasma and cellular factors including coagulation factors, and complement activation fragments, bradykinin system components, platelets and platelet factor 4, and integrin-adhesin interactions.

To evaluate the possible cellular mechanisms through which MGDG-EPA microalgal lipid preparations may exert their effects in croton oil-induced mouse ear swelling, ears were excised from the euthanized mice of EXAMPLE 4, above, and preserved in 10% formalin. Specimens were dehydrated in alcohol, cleared with xylene, imbedded in paraffin, sectioned and stained with hematoxylin-eosin. Sections were cut at different locations in each ear. Hematoxylin-eosin stained cross-sections of mouse ears were examined microscopically at 100X, 400X, and 100X magnification. Comparisons were made to the histology of normal untreated unchallenged mouse ears.

Inflammation induced by croton oil in control animals: Normal (control) mice challenged with croton oil exhibited the following histology. Namely, normal epithelial histology was disrupted with stretching of the epithelium to just 2 cells thickness in some locations and an increased cross-sectional area relative to normal control ears. Neutrophil infiltration was prominent in the connective tissue layer underlying the epithelium, and in the microvasculature of the ears (i.e., pavementing).

Prophylaxis with MGDG-EPA: Mice pretreated with gel emollient containing MGDG-EPA exhibited a normal epithelial histology with little to no evidence of neutrophil infiltration or pavementing in the microvasculature.

The results of these histologic studies suggest that pretreatment with MGDG-EPA inhibits the induction phase of inflammation, as evidenced by a near complete lack of neutrophils in treated tissues. Thus, measurements of ear swelling and histology indicate that rather than inhibiting ongoing inflammatory events, (e.g., production of inflammatory arachidonic acid metabolites by neutrophils), the prophylactic treatment with MGDG-EPA appeared to inhibit the induction phase of inflammation, i.e., triggering and/or recruitment of inflammatory cells into the croton oil treated tissues.

EXAMPLE 7

Treatments with MGDG-EPA Compositions Ameliorate Acute UV Induced Skin Damage

Acute UV exposure model: Exposure of the dorsal shaved skin of mice to acute UV results in skin lesions that are hyperplastic and with keratosis. The effects of a topical anti-inflammatory composition containing 5% MGDG-EPA microalgal lipid in a petrolatum base was evaluated by applying the composition to the dorsal shaved skin of 25 female Balb/c mice (5 weeks of age) twice daily on each of 6 consecutive days. An equal number of mice in a control group received only the petrolatum base, i.e., 0% MGDG-EPA. On the eighth day after treatment was applied, an acute dose of ultraviolet light was administered to the dorsal skin. Prophylactic treatments with the MGDG-EPA containing microalgal lipid preparation significantly decreased the incidence of hyperplastic skin lesions, i.e., only 1 of 25 mice (4%) treated with MGDG-EPA exhibited skin lesions as compared with 7 of 25 mice (28%) in the control group ($p=0.018$).

EXAMPLE 8

Therapeutic Treatment of Pruritic Skin Disease in Dogs

The experiments in Examples 3–7, above illustrate results obtained in chemically induced and UV induced inflammation models. As a third inflammatory model, allergic inflammation, i.e., type 1 hypersensitivity, was investigated in veterinary treatment of canine atopic dermatitis, (normally treated with immunosuppressants including corticosteroids). A 'single-blind', 'placebo-controlled'open clinical trial was performed by instructing dog owners in the treatment of different marked dermal sites with one of two different emollient gels, i.e., either a control or an experimental gel. The trial was conducted under the supervision of a diplomat of the American College of Veterinary Dermatology and a specialist in small animal skin disorders.

Case Report #1: The first test subject was a spaniel who presented with pruritic atopic dermatitis and who had been under care for about 2.5 years with treatments including oral corticosteroids, essential fatty acids, and various topical shampoos. Corticosteroids were effective in controlling the disease, but use was accompanied with the usual risks. Upon presentation for inclusion in the trial, the dog exhibited an exacerbation of the allergic condition with lesions having moist, eroded papular dermatitis.. Four pruritic areas, each about 3–5 cm in diameter were selected, three were treated using the MGDG-EPA gel and one remained as a vehicle-only treated control site. The subject lesions were marked and the owner was given instruction in the twice daily application of either Gel #1 (Sites #1 and #2), Gel #2 (Site #3), or Gel #3 (Site #4): i.e., Gel #1: experimental, 1% MGDG-EPA-containing microalgal lipid preparation (95% pure) in a gel emollient; Gel #2: experimental, 2% MGDG-EPA-containing microalgal lipid preparation (95% pure) in a gel emollient; and, Gel #3: control, gel base. The owner was not told the identity of the compositions.

The subject was examined by the veterinarian on a biweekly schedule during the trial. The owner reported that 3 applications at Sites #1–#3, i.e., Gels #1 and #2 eliminated scratching and biting, while continuing skin irritation was observed at Site #4. Veterinary records indicated reduction in erythema at Sites #1–#3 by the first biweekly visit, and a complete elimination of erythema at these sites within 4 weeks with renewed hair growth being evident. In contrast, control Site #4 showed minimal reduction in erythema after 4 weeks. Multiple other (unmarked) sites on this animal evidenced continued systemic allergic disease activity.

Case Report #2: The second test subject was a German shepherd/golden retriever mix who presented with allergic dermatitis from fleas.

Three pruritic areas, each about 3–5 cm in diameter were selected, shaved and marked. The owner was given instruction in the twice daily application of either Gel #1 (Site #1), Gel #2 (Site #2), or Gel #3 (Site #3): i.e., Gel #1: experimental, 1% MGDG-EPA containing microalgal lipid preparation (95% pure) in a gel emollient; Gel #2: experimental, 2% MGDG-EPA containing microalgal lipid preparation (95% pure) in a gel emollient, and, Gel #3: control, gel base. The owner was not told the identity of the compositions.

The subject was examined by the veterinarian on a biweekly interval and the following results were recorded (TABLE 12).

TABLE 12

Treatment of Atopic Dermatitis: Reduction in Inflammation*

| Site # | Treatment | start | 1st biweek | 2nd. biweek |
|---|---|---|---|---|
| 1 | 1% MGDG—EPA gel | 4+ | 2+ | 1+ |
| 2 | 2% MGDG—EPA gel | 4+ | 3+ | 2+ |
| 3 | Gel control | 4+ | 4+ | 4+ |

*Erythema scored on a 4+ scale where: 4+, strong; 3+, moderate; 2+ mild; 1+ negligible The results obtained in veterinary treatment of these two animals confirm and extend the results presented above with experimental animals, since they indicate utility of MGDG-EPA containing microalgal lipid preparations in emollient formulations for treating atopic allergic dermatitis.

In Summary: The results presented in EXAMPLES 1–8, above, show purification and formulation from natural materials of a topical anti-inflammatory "microalgal lipid preparation" that exhibits activity in both prophylactic and therapeutic treatment regimens. Although the composition contains eicosapentaenoic acids, and the observed anti-inflammatory activities appear to function (at least in part) by preventing neutrophil infiltration during the induction phase of an inflammatory response, the mode of action appears incompatible with a classical substrate-substitution model in which EPA replaces arachidonic acid in the eicosanoid pathway. Purity of the microalgal lipid preparation appears to be key, as contaminants present in natural algal extracts can potentiate inflammation and nullify any observed effects of the composition.

Materials and Methods for Examples 1–8 (above)

Lipids: Certain of the following lipids were purified (or where indicated purchased) for use in the preceding studies: namely, monogalactosyl dieicosapentaenoyl glycerol purified to 96% purity from marine microalgae, abbreviated MGDG-EPA; 81% 20:5 (EPA) fatty acids in the preparation as percentage of total fatty acids in the lipid preparation;

eicosapentaenoyl phosphatidylethanolamine and phosphatidyl glycerol, abbreviated PE/PG-EPA, purified from marine microalgae 53% 20:5 (EPA) fatty acid in the preparation as percentage of total fatty acids in the lipid preparation;

monogalactosyl diacylglycerol purified to 95% from spinach; 75% 18:3 and 25% 16:3 fatty acids in the preparation as percentage of total fatty acids in the lipid preparation;

dieicosapentaenoylglyceryl-N,N,N-trimethylhomoserine purified to 98% from marine microalgae, abbreviated DGTS-EPA; 90% 20:5 (EPA) fatty acid as percentage of total fatty acids in the lipid preparation;

EPA-ethyl ester, 93% 20:5 (EPA) fatty acid as percentage of total weight of the lipid preparation; obtained from the National Marine Fisheries Service, Charleston, SC;

1-palmitoyl, 2-arachidonyl phosphatidylethanolamine purchased from Avanti Lipids, Alabaster, AL; and, Fish oil was obtained from Croda Corp., Hull, England, i.e., Incromega 3TG60 from Menhaden; 36% 20:5 (EPA) fatty acid and 24% docosahexaenoic acid 22:6-n3 as percentage of total weight of the lipid preparation.

All of the preceding lipid preparations were>90% pure as assessed by TLC and/or HPLC. The<10% contaminants present in the algal preparations include other EPA-containing lipids and traces of chlorophyll analogues and carotenoids. Contaminants in the 96% pure MGDG-EPA preparation included 2% polar lipids including DGTS-EPA and 2% chlorophylls, i.e., 96:2:2.

TLC: Purity was assessed by TLC or HPLC. The TLC solvent system was 10% methanol in chloroform and the stationary phase was silica gel.

Formulation into a emmollient: Algal-lipid formulations were prepared in petrolatum or aqueous gel (below) at desired test concentrations, above.

Aqueous gel emollient: The water-washable, pH neutral, gel emollient used in the preceding EXAMPLES was formulated (% weight) as follows: namely, 1% microalgal lipid preparation, 65.2% deionized water, 0.2% Carbopol 940NF (Goodrich), 11.2% L-Sorbitol (Spectrum), 0.4% sodium hydroxymethyl glycinate (Sutton), 7.0% myristyl proprionate (Lonza), 4% mineral oil (Penreco), 0.5% Aloe Vera oil, 0.1% retinol palmitate (Sigma), 0.2% dl-Tocopheryl acetate (Spectrum), 0.2% L-ascorbate-6-palmitate (Sigma), 6% stearic acid (Spectrum), 4% glyceryl monostearate (Spectrum), trace fragrance (Cromptom).

Control anti-inflammatory agent: 0.05% betamethasone dipropionate lotion, a synthetic corticosteroid analogue, was manufactured by Schering Corporation, Kenilworth, N.J.

Inflammation Animal Model Materials: Croton oil was purchased from Sigma Chemical Co., St. Louis, MO. Female Balb/c mice (aged 12–16 weeks) were purchased from the animal facility of the National Cancer Institute. Sample groups were constituted of 6–10 ears.

Inflammation Animal Model: Mouse ears were treated on the back side on each of five consecutive days with approximately 6 μl of petrolatum or gel containing test lipids at 8:00 and 16:00 each day. Inflammation was induced using a solution of 10% croton oil in acetone on day 5. An even thin coat of each test formulation was applied from a pre-weighed container with a pre-weighed wooden-stick applicator. The applicator was then wrapped in a pre-weighed gauze sponge and the exact dosage applied to each group of animal was later determined by weighing. Inflammatory challenge with croton oil consisted of 10 μl of 10% croton oil in acetone applied to the back of each ear. Ear thickness was measured in different experiments before treatment (baseline) and at 0, 8, 24 and/or 48 hr. after challenge using a Mitutoyo #7305 spring loaded ear thickness micrometer having a measuring surface of 1 cm diameter, i.e., approximately the size of the mouse ear. Maximal ear thickness was achieved at 24 hr. Swelling was determined as the difference in ear thickness between the baseline value and value recorded at the later time. Results were analyzed using either Student's t-test or the Wilcoxon Rank Sum Test, where significance in the difference between the means was accepted at $p<0.05$.

Where ear biopsy weight is indicated, the biopsy samples were obtained, after euthanizing the animal, with a 3 mm dermal punch to excise a full thickness of the ear. Biopsy weights were determined using an analytical balance.

Citations

1. Chandra, R. K. (Ed.) (1989) *Health Effects of Fish and Fish Oils.* ARTS, Biomedical Publishers and Distributors, St Johns, Newfoundland, Canada.

2. Calder, P. C. and Newsholme, E.A. (1992) Polyunsaturated fatty acids suppress human peripheral blood lymphocyte proliferation and interleukin-2 production. Clin. Sci. 82: 695–700.

3. Holub, B. J., Celi, B. and Skeaff, C. M. (1988) The alkenyl class of ethanolamine phospholipid represents a major form of eicosapentaenoic acid (EPA)-containing phospholipid in the platelets of human subjects consuming a fish oil concentrate. Thromb. Res. 50: 135–143.

4. Henderson, W. R. (1988) *Eicosanoids and lung inflammation.* Am. Rev. Respir.Dis. 135: 1176–1185.

5. Leitch, A. G., Lee, T. H., Ringel, E. W., Prickett, J. D., Robinson, D. R., Pyne, S. G., Corey, E. J., Drazen, J. M., Austen, K. F., and Lewis, R. A. (1984) Immunologically induced generation of tetraene and pentaene leukotrienes in the peritoneal cavities of menhaden-fed rats. J. Immunol. 132: 2559–2565.

6. Terano, T., Salmon, J. A., Higgs, G. A. and Moncada, S. (1986) Eicosapentaenoic acid as a modulator of inflammation. Biochem. Pharmacol. 35: 779–785.

7. Krueger, G. G., Jorgenson, C. M., Haigh, W. G. and Winget, R. R. (1992) Percutaneous absorption and anti-inflammatory activity of topically applied lipids containing either arachidonic acid or eicosapentaenoic acid. Clin. Res. 40: 164A.

While the preferred embodiment of the invention has been illustrated and described, it will be appreciated that various changes can be made therein without departing from the spirit and scope of the invention.

I claim:

1. A topical dermal anti-inflammatory composition comprising about 0.1 percent to about 10 percent by weight of an anti-inflammatory microalgal lipid preparation and a vehicle comprising the remaining percent by weight, wherein the anti-inflammatory microalgal lipid preparation comprises 35 percent to 100 percent by weight of a monogalactosyl dieicosapentaenoyl glycerol having the structure:

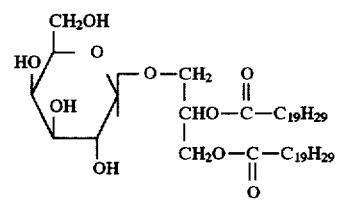

wherein $C_{19}H_{29}$ represents the unsaturated hydrocarbon chain of the eicosapentaenoic acid having 5 carbon-carbon double bonds, and wherein the anti-inflammatory microalgal lipid preparation comprises between 0% and about 65% by weight of at least one contaminant, wherein the contaminant is selected from the group consisting of a diacylglyceryl-N,N,N-trimethylhomoserine, a chlorophyll, a carotenoid and phospholipids, and wherein the vehicle is selected from the group consisting of an ointment, a cream, a lotion, an emollient and a bioadhesive delivery system.

2. The composition of claim 1 wherein the anti-inflammatory microalgal lipid preparation comprises monogalactosyl dieicosapentaenoyl glycerol in an amount ranging from 85 percent to 95 percent by weight of the preparation and wherein the contaminants comprise between 0% and about 15 percent by weight of the composition.

3. The composition of claim 1 wherein the emollient comprises a water washable pH neutral aqueous gel.

4. The composition of claim 1 wherein the anti-inflammatory microalgal lipid preparation further comprises a digalactosyldiacylglycerol having the structure:

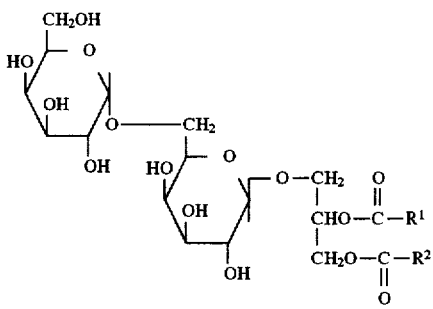

wherein $R^1$ and $R^2$ represent the hydrocarbon chain of a fatty acid comprising from 10 to 25 carbon atoms and from 0 to 6 carbon-carbon double bonds.

5. An anti-inflammatory aqueous pharmaceutical solution comprising about 0.1 percent to about 10 percent by weight of an anti-inflammatory microalgal lipid preparation, the remaining percent by weight comprising a buffer salt, a stabilizer or a preservative, wherein the anti-inflammatory microalgal lipid preparation comprises 35 percent to 100 percent by weight of a monogalactosyl dieicosapentaenoyl glycerol having the structure:

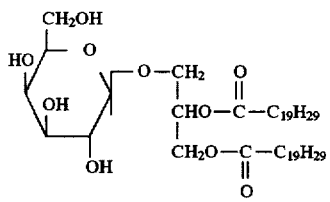

wherein $C_{19}H_{29}$ represents the unsaturated hydrocarbon chain of the eicosapentaenoic acid having 5 carbon-carbon double bonds, and wherein the anti-inflammatory microalgal lipid preparation comprises between 0% and about 65% by weight of at least one contaminant, wherein the contaminant is selected from the group consisting of a diacylglyceryl-N,N,N-trimethylhomoserine, a chlorophyll, a carotenoid and phospholipids, and wherein the anti-inflammatory aqueous solution comprises a stable homogenous solution that does not contain an organic solvent.

6. The aqueous pharmaceutical solution of claim 5 wherein the anti-inflammatory microalgal lipid preparation comprises monogalactosyl dieicosapentaenoyl glycerol in an amount ranging from 85 percent to 95 percent by weight of the preparation and wherein the contaminants comprise between 0% and about 15 percent by weight of the composition.

7. The aqueous pharmaceutal solution of claim 5 wherein the anti-inflammatory microalgal lipid preparation further comprises a digalactosyldiacylglycerol having the structure:

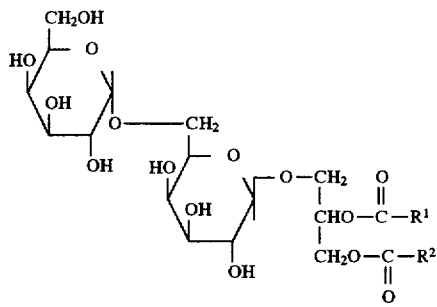

wherein $R^1$ and $R^2$ represent the hydrocarbon chain of a fatty acid comprising from 10 to 25 carbon atoms and from 0 to 6 carbon-carbon double bonds.

8. A process of manufacturing an anti-inflammatory microalgal lipid preparation, comprising the steps of:

extracting alga with an extraction solvent to yield an extract;

phase separating the extract with an organic water-immiscible solvent and water to yield an organic phase;

fractionating the organic phase by polar chromatographic separation employing deactivated alumina with a first fractionating solvent to yield an enriched glycolipid fraction;

fractionating the enriched glycolipid fraction by a second polar chromatographic separation with a second fractionating solvent to yield a further enriched diglyceride fraction; and removing solvents from the further enriched glycolipid fraction to yield the monogalactosyl dieicosapentaenoyl glycerol;

wherein the anti-inflammatory microalgal lipid preparation comprises 35 percent to 100 percent by weight of a monogalactosyl dieicosapentaenoyl glycerol having the structure:

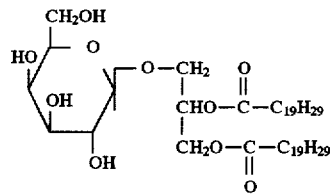

wherein $C_{19}H_{29}$ represents the unsaturated hydrocarbon chain of the eicosapentaenoic acid having 5 carbon-carbon double bonds, and wherein the anti-inflammatory microalgal lipid preparation comprises between 0% and about 65% by weight of at least one contaminant, wherein the contaminant is selected from the group consisting of a diacylglyceryl-N,N,N-trimethylhomoserine, a chlorophyll, a carotenoid and phospholipids.

9. The process of claim 8 wherein the alga is selected from the genera comprising Chlorella, Chaetoceros, Cyclotella, Isochrysis, Nannochloropis, Nitzschia and Phyacodactylum, or from the species comprising *Chlorella minutissima, Chaetoceros gracillis, Chaetoceros muelleri, Cyclotella creptica, Isochrysis galbana, Nannochloropsis salina, Nitzschia dissipata* and *Phyaeodactylum tricornutum.*

10. The process of claim 8 wherein the organic water-immiscible solvent is selected from the group consisting of hydrocarbons, ethers, and chlorinated hydrocarbons, or from the group consisting of pentane, hexane, petroleum ethers, diethyl ether, dichloromethane and chloroform.

11. The process of claim 8 wherein the first fractionating solvent is selected from the group consisting of polar organic solvents, non-polar organic solvents, mixtures thereof, and mixtures thereof containing water, or from the group consisting of alcohols and esters, or from the group consisting of methanol, ethanol and ethyl acetate, or from the group consisting of hydrocarbons, petroleum ethers and chlorinated hydrocarbons, or from the group consisting of pentane, hexane, diethyl ether, dichloromethane and chloroform.

12. The process of claim 8 wherein the first fractionating solvent comprises a mixture of ethanol, hexanes and water.

13. The process of claim 8 wherein the second fractionating solvent comprises a mixture of ethanol and hexane.

14. The process of claim 8 wherein the extraction solvent comprises a polar organic solvent selected from the group consisting of alcohols, esters, ethers, ketones, aldehydes, mixtures thereof, and mixtures thereof containing water, or from the group consisting of methanol, ethanol, propanol, isopropanol, acetone, mixtures thereof, and mixtures thereof containing water.

15. The process of claim 14 wherein the extraction solvent comprises 90% aqueous ethanol.

* * * * *